US010261045B2

(12) United States Patent
Kawamoto et al.

(10) Patent No.: US 10,261,045 B2
(45) Date of Patent: Apr. 16, 2019

(54) GAS SENSOR

(71) Applicant: DENSO CORPORATION, Kariya, Aichi-pref. (JP)

(72) Inventors: Yuusuke Kawamoto, Kariya (JP); Yuusuke Toudou, Kariya (JP)

(73) Assignee: DENSO CORPORATION, Kariya (JP)

( * ) Notice: Subject to any disclaimer, the term of this patent is extended or adjusted under 35 U.S.C. 154(b) by 159 days.

(21) Appl. No.: 15/319,128

(22) PCT Filed: Jun. 15, 2015

(86) PCT No.: PCT/JP2015/067117
§ 371 (c)(1),
(2) Date: Dec. 15, 2016

(87) PCT Pub. No.: WO2015/194490
PCT Pub. Date: Dec. 23, 2015

(65) Prior Publication Data
US 2017/0122897 A1    May 4, 2017

(30) Foreign Application Priority Data

Jun. 16, 2014   (JP) .................................. 2014-123454
Mar. 26, 2015   (JP) .................................. 2015-064273

(51) Int. Cl.
*G01N 27/407*  (2006.01)
*G01N 27/41*   (2006.01)
(Continued)

(52) U.S. Cl.
CPC ....... *G01N 27/409* (2013.01); *G01N 27/4067* (2013.01); *G01N 27/4075* (2013.01); *G01N 27/41* (2013.01)

(58) Field of Classification Search
CPC ... G01N 27/409; G01N 27/41; G01N 27/4067
See application file for complete search history.

(56) References Cited

U.S. PATENT DOCUMENTS 4,347,113 A * 8/1982 Fischer .............. G01N 27/4075
                                                  204/428
5,997,707 A * 12/1999 Kato .................... G01N 27/419
                                                  204/425
(Continued)

FOREIGN PATENT DOCUMENTS

JP        2003-065999        3/2003

*Primary Examiner* — Alexander S Noguerola
(74) *Attorney, Agent, or Firm* — Nixon & Vanderhye P.C.

(57) ABSTRACT

A sensor structural body, which is formed by stacking a sensor element and a heater, has a sensor protruding portion that protrudes distalward from a holder. The sensor element includes a solid electrolyte body, a measured-gas space, a reference-gas space, a pump cell, a monitor cell and a sensor cell. A heat-generating portion of the heater is entirely arranged in the sensor protruding portion. The length L (in mm) of a formation region of the heat-generating portion and the length H (in mm) of the sensor protruding portion in a longitudinal direction, in which the sensor protruding portion protrudes from the holder, are set to be in a range that is enclosed by first to fourth reference lines X1, X2, X3 and X4 on a two-dimensional coordinate plane whose horizontal and vertical axes respectively indicate the lengths L and H. The first to the fourth reference lines X1-X4 respectively represent the relationships of H=L, H=20, H=−4.24L+42.71 and H=−4.24L+68.6.

4 Claims, 8 Drawing Sheets

(51) Int. Cl.
*G01N 27/409* (2006.01)
*G01N 27/406* (2006.01)

(56) References Cited

U.S. PATENT DOCUMENTS

| | | | | |
|---|---|---|---|---|
| 6,068,747 | A * | 5/2000 | Tojo | G01N 27/417 204/425 |
| 6,319,377 | B1 * | 11/2001 | Hasei | G01N 27/417 204/425 |
| 2008/0289961 | A1 * | 11/2008 | Schmitt | G01N 27/4071 204/424 |
| 2009/0308748 | A1 * | 12/2009 | Wahl | G01N 27/4067 204/424 |

* cited by examiner

GAS SENSOR

This application is the U.S. national phase of International Application No. PCT/JP2015/067117 filed 15 Jun. 2015 which designated the U.S. and claims priority to JP Patent Application No. 2014-123454 filed 16 Jun. 2014 and JP Patent Application No. 2015-064273 filed 26 Mar. 2015, the entire contents of each of which are hereby incorporated by reference.

TECHNICAL FIELD

The present invention relates to gas sensors that sense a specific gas concentration in exhaust gas.

BACKGROUND ART

Gas sensors are arranged in an exhaust pipe of an internal combustion engine and used to sense a specific gas concentration in exhaust gas flowing in the exhaust pipe. In the gas sensors, a sensor structural body, which is formed by stacking a heater on a sensor element, is held by a holder; a distal end portion of the sensor structural body is protruded from the holder so as to be exposed to a measured gas. The heater is provided to heat a solid electrolyte body and electrodes provided on the solid electrolyte body to a sensor activation temperature. Specifically, the heater is formed by providing an electric conductor layer on a ceramic substrate; the electric conductor layer generates heat when supplied with electric current. Moreover, in the sensor element, there are formed: a pump cell that adjusts the oxygen concentration in the exhaust gas which is the measured gas; and a sensor cell for sensing the specific gas concentration of the measured gas whose oxygen concentration has been adjusted by the pump cell.

For example, a gas sensor element disclosed in Patent Document 1 has a heater portion which includes a heat-generating element that generates heat when supplied with electric current. Moreover, in Patent Document 1, it is disclosed that the heater voltage is regulated so as to have the relationship between heater resistance and heater electric power satisfying a heater control function, thereby controlling the temperature of the gas sensor element.

PRIOR ART LITERATURE

Patent Literature

[PATENT DOCUMENT 1] Japanese Patent Application Publication No. JP2003065999A

SUMMARY OF THE INVENTION

Problems to be Solved by the Invention

In Patent Document 1, it is aimed to control the temperature of the gas sensor element (or sensor element). However, the required functions of the pump cell and the sensor cell are different from each other, and the materials of electrodes constituting the pump cell and the sensor cell are also different from each other. Therefore, the optimal temperatures (or the activation temperatures of the electrodes) for controlling the pump cell and the sensor cell are also different from each other. Accordingly, the structural arrangement relationships in the sensor element are critical to controlling a plurality of cells, such as the pump cell and the sensor cell, to the respective optimal temperatures.

Specifically, it has been made clear that the relationship between the length of a formation region of the heat-generating portion in the electric conductor layer of the heater and the protruding length of the distal end portion of the sensor structural body from the holder is critical. That is, it has been made clear that: the heat of the sensor structural body heated by the heater escapes to the holder whose temperature is lower than that of the sensor structural body; and it is therefore impossible to suitably control the temperatures of the pump cell and the sensor cell if the protruding length of the distal end portion of the sensor structural body from the holder is not suitably set.

The present invention has been made in view of the above circumstances, and aims to provide a gas sensor capable of suitably controlling the temperatures of a pump cell and a sensor cell.

Means for Solving the Problems

A gas sensor according to the present invention has a sensor structural body formed by stacking a sensor element and a heater and a holder holding the sensor structural body. The gas sensor is configured so that a sensor protruding portion of the sensor structural body protrudes distalward from the holder so as to be exposed to a measured gas. The sensor element includes: a solid electrolyte body having oxygen ion conductivity; a measured-gas space which is formed on one side of the solid electrolyte body and into which the measured gas is introduced via a diffusion-resistant body; a reference-gas space which is formed on the other side of the solid electrolyte body and into which a reference gas is introduced; a pump cell having a pump electrode provided on a measured-gas space-side surface of the solid electrolyte body and being configured to adjust the concentration of oxygen in the measured-gas space by applying a voltage between the pump electrode and a reference electrode provided on a reference-gas space-side surface of the solid electrolyte body; and a sensor cell having a sensor electrode provided on the measured-gas space-side surface of the solid electrolyte body and proximalward from the arrangement position of the pump electrode, the sensor cell being configured to measure oxygen ion current flowing between the sensor electrode and the reference electrode. The heater includes a heat-generating portion that generates heat when supplied with electric current, and a pair of lead portions that are respectively connected with a pair of end portions of the heat-generating portion. The entire heat-generating portion is arranged in the sensor protruding portion. A heat-generating center of the heat-generating portion is located distalward from a center of the sensor electrode. A distance E from a distal end of the sensor protruding portion to the center of the sensor electrode is in a range of 0.7 to 1.3 D and a distance F from the distal end of the sensor protruding portion to a center of the pump electrode is in a range of 0.3 to 0.7 D, where D is a distance from the distal end of the sensor protruding portion to a proximal end of the heat-generating portion. A length L (in mm) of a formation region of the heat-generating portion and a length H (in mm) of the sensor protruding portion in a longitudinal direction, in which the sensor protruding portion protrudes from the holder, are set to be in a range that is enclosed by first to fourth reference lines on a two-dimensional coordinate plane whose horizontal and vertical axes respectively indicate the lengths L and H. The first reference line represents a relationship of H=L. The second reference line represents a relationship of H=20. The third reference line represents the relationship of $H=-4.24L+42.71$. The fourth reference line represents the relationship of $H=-4.24L+68.6$.

Advantageous Effects of the Invention

In the above gas sensor, there is specified a suitable range of the length L (in mm) of the formation region of the heat-generating portion and the length H (in mm) of the sensor protruding portion in the direction in which the sensor protruding portion protrudes from the holder.

Specifically, the length L (in mm) of the formation region of the heat-generating portion and the length H (in mm) of the sensor protruding portion are set to be in the range that is enclosed by the first to the fourth reference lines on the two-dimensional coordinate plane whose horizontal and vertical axes respectively indicate the lengths L and H. The first to the fourth reference lines respectively represent the relationships of $H=L$, $H=20$, $H=-4.24L+42.71$ and $H=-4.24L+68.6$. Consequently, in heating the solid electrolyte body, the pump electrode, the sensor electrode and the reference electrode by the heater, it is possible to keep the temperature of the pump cell in a suitable range of higher than or equal to 740° C. and the temperature of the sensor cell in a suitable range of 650 to 830° C. Here, the temperature of the pump cell denotes the temperature of the pump electrode in the measured-gas space and the temperature of the sensor cell denotes the temperature of the sensor electrode in the measured-gas space.

Accordingly, the above gas sensor can suitably control the temperatures of the pump cell and the sensor cell.

In addition, if the temperature of the pump cell drops below 740° C., it becomes impossible for the pump cell to sufficiently exhaust oxygen, lowering the accuracy of sensing a specific gas concentration in the measured gas. On the other hand, if the temperature of the sensor cell exceeds 830° C., the sensor cell comes to sense moisture in the measured gas, lowering the accuracy of sensing the specific gas concentration in the measured gas.

EMBODIMENTS FOR CARRYING OUT THE INVENTION

Preferred embodiments of the above gas sensor will be described hereinafter.

The above gas sensor may further include a monitor cell that measures the residual oxygen concentration in the measured gas whose oxygen concentration has been adjusted by the pump cell. The monitor cell may have a monitor electrode provided on the measured-gas space-side surface of the solid electrolyte body and in alignment with the sensor electrode in a width direction perpendicular to the longitudinal direction. The monitor cell may be configured to measure oxygen ion current flowing between the monitor electrode and the reference electrode.

If the above distance E is shorter than 0.7 D, the length of the formation region of the heat-generating portion becomes too large, lowering the efficiency of heating the sensor element by the heater. On the other hand, if the above distance E is longer than 1.3 D, the length of the formation region of the heat-generating portion becomes too short, making it impossible to suitably control the temperature of the sensor electrode.

If the above distance F is shorter than 0.3 D, the efficiency of heating the sensor element by the heater is lowered. On the other hand, if the above distance F is longer than 0.7 D, it becomes impossible to suitably control the temperature of the pump electrode.

In addition, in the above gas sensor, the "distal side" denotes one side in the longitudinal direction of the gas sensor (i.e., the longitudinal direction in which the sensor protruding portion protrudes from the holder) where the gas sensor is to be exposed to the measured gas. Moreover, the "proximal side" denotes the opposite side to the distal side.

EXAMPLE

Hereinafter, a gas sensor 1 according to an example will be described with reference to FIGS. 1-12.

Figure 1:
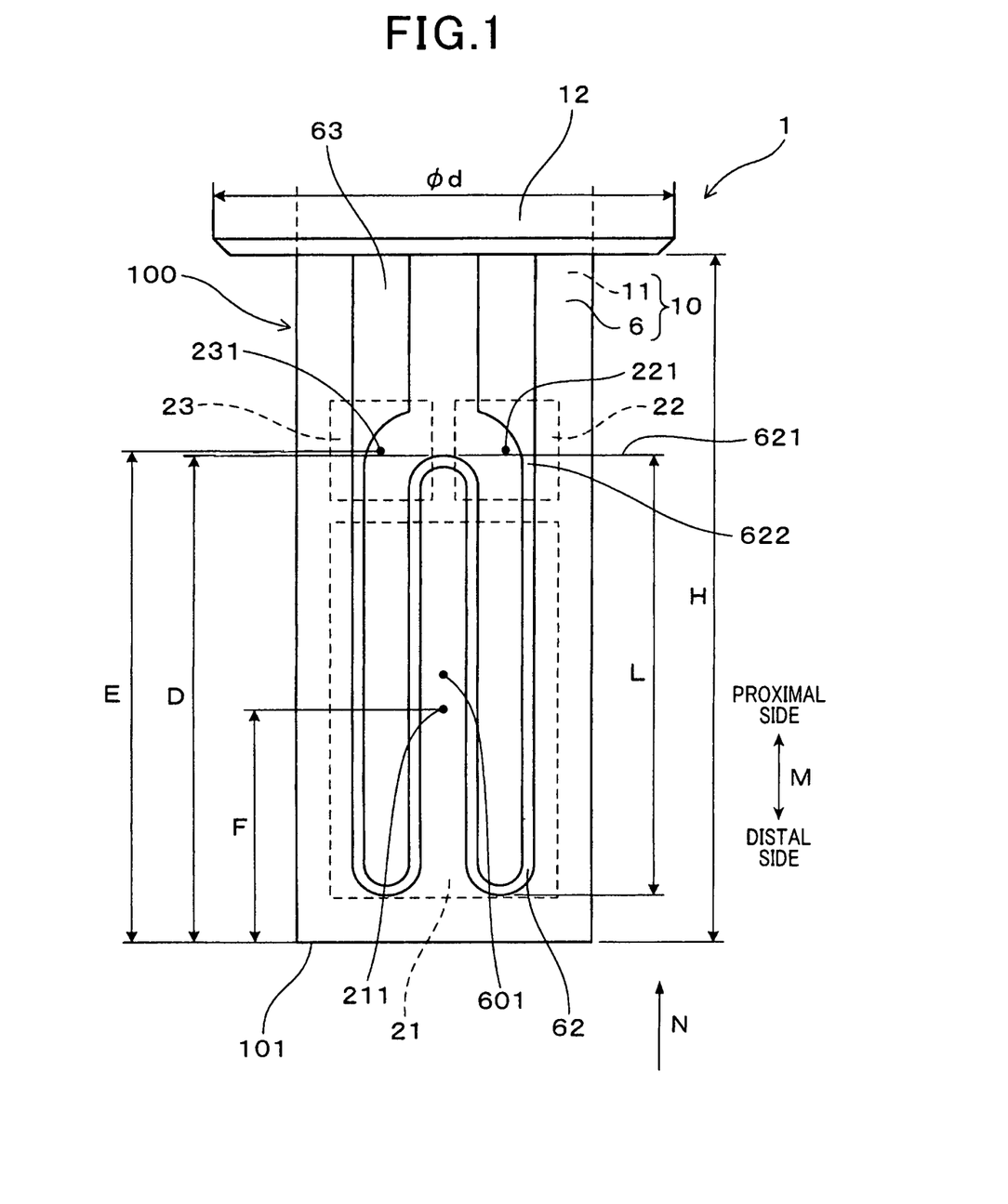
FIG. 1 is a schematic view showing a distal end portion of a gas sensor according to an example.
Figure 4:
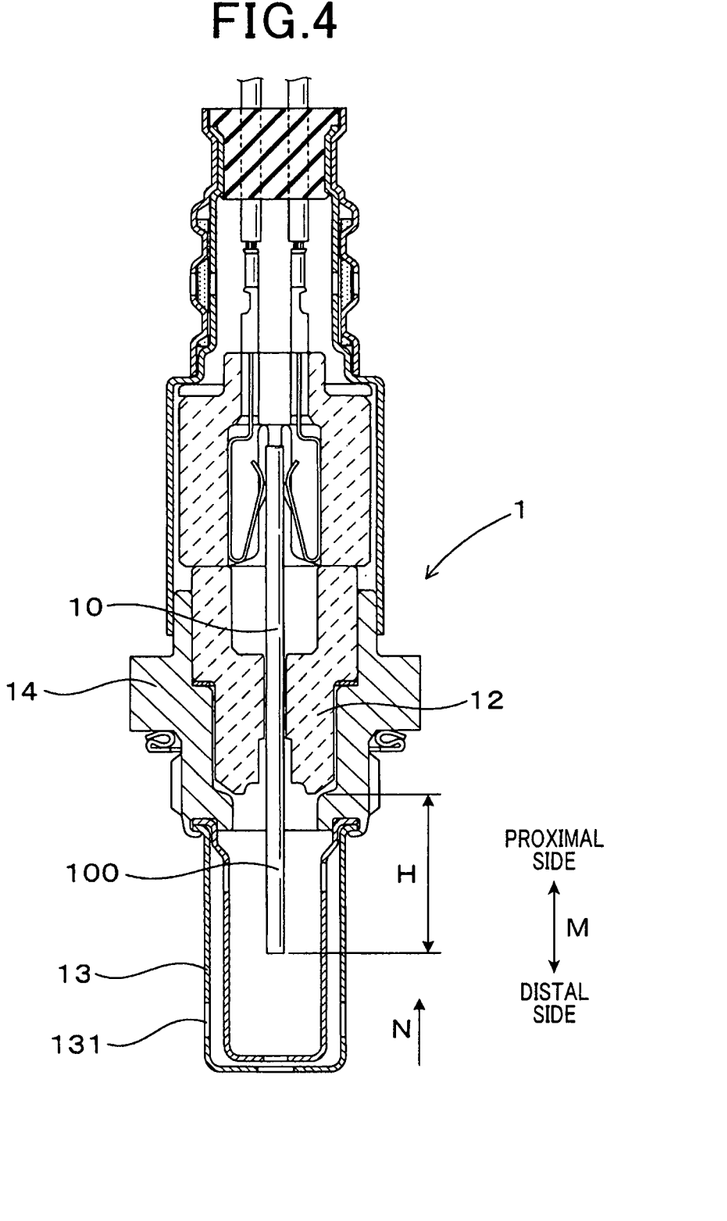
FIG. 4 is a cross-sectional view of the entire gas sensor according to the example.

As shown in FIGS. 1 and 4, the gas sensor 1 according to the present example includes a sensor structural body 10 that is formed by stacking a sensor element 11 and a heater 6, and a holder 12 that holds the sensor structural body 10. A distal end portion of the sensor structural body 10 in a longitudinal direction M constitutes a sensor protruding portion 100 that protrudes distalward from the holder 12. The sensor protruding portion 100 is a portion which is to be exposed to a measured gas G.

Figure 2:
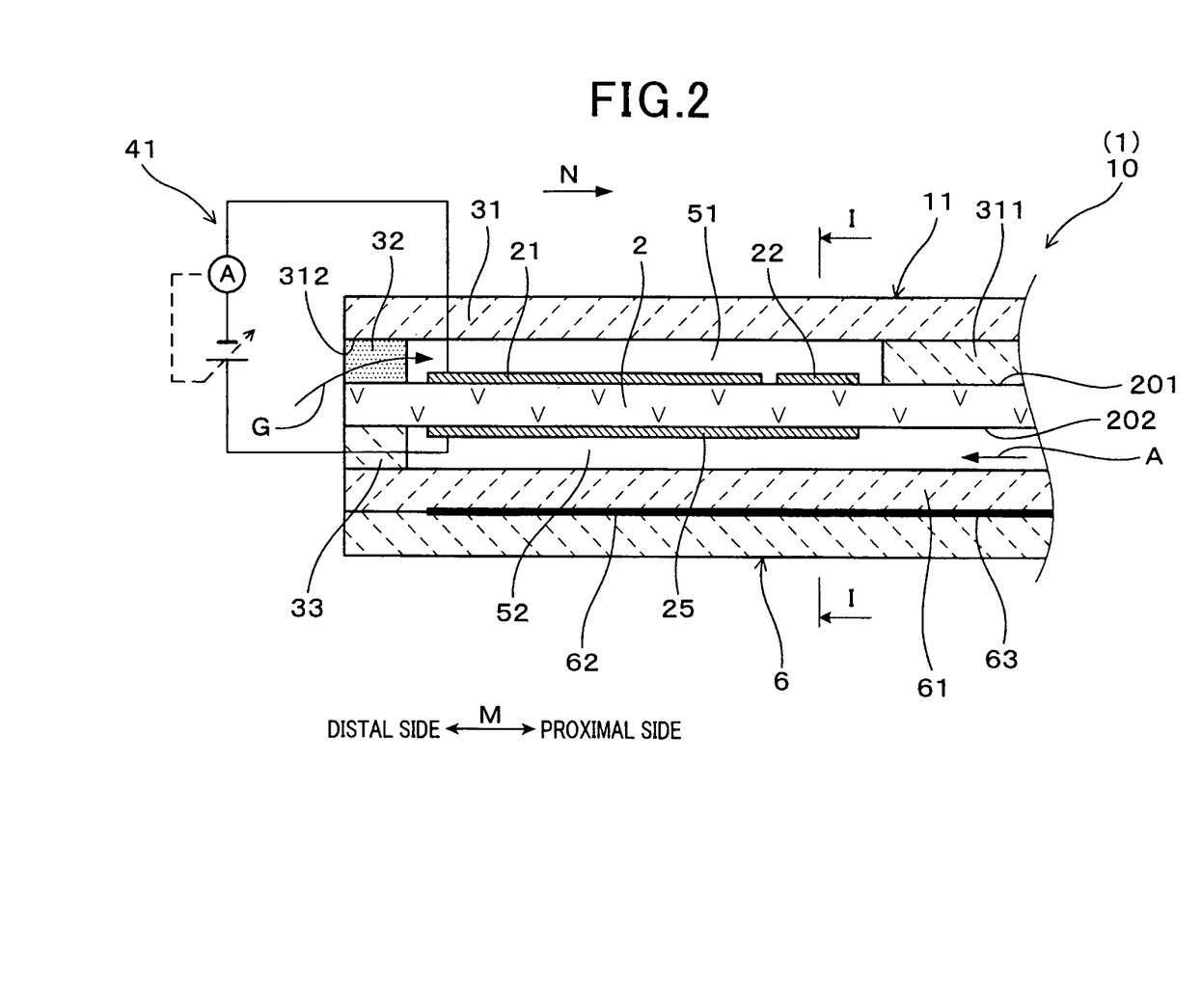
FIG. 2 is a cross-sectional view showing a sensor protruding portion of a sensor structural body of the gas sensor according to the example.
Figure 3:
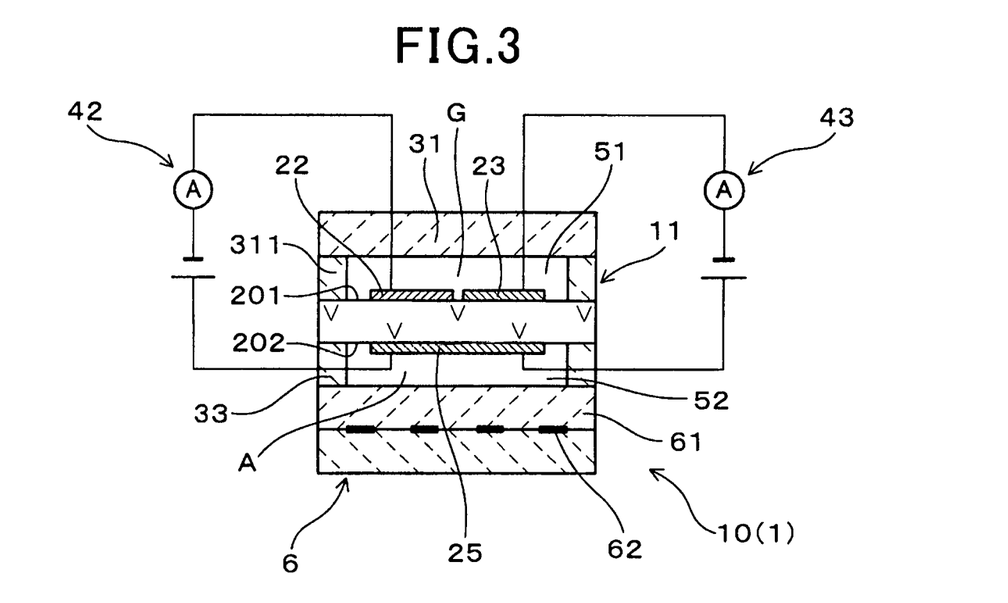
FIG. 3 is a cross-sectional view taken along the line I-I in FIG. 2.

As shown in FIGS. 2 and 3, the sensor element 11 includes a solid electrolyte body 2 having oxygen ion conductivity, a measured-gas space 51, a reference-gas space 52, a pump cell 41, a monitor cell 42 and a sensor cell 43. The measured-gas space 51 is formed, on one side of the solid electrolyte body 2, as a space into which exhaust gas is introduced as the measured gas G through a diffusion-resistant body 32. The reference-gas space 52 is formed, on the other side of the solid electrolyte body 2, as a space into which a reference gas A is introduced. The pump cell 41 has a pump electrode 21 provided on a measured-gas space 51-side surface 201 of the solid electrolyte body 2. The pump cell 41 is configured to adjust the oxygen concentration in the measured-gas space 51 by applying a voltage between the pump electrode 21 and a reference electrode 25 provided on a reference-gas space 52-side surface 202 of the solid electrolyte body 2.

The monitor cell 42 has a monitor electrode 22 provided on the measured-gas space 51-side surface 201 of the solid electrolyte body 2 and in alignment with a sensor electrode 23 in a width direction perpendicular to the longitudinal direction M. The monitor cell 42 is configured to measure the oxygen ion current flowing between the monitor electrode 22 and the reference electrode 25 and thereby measure the residual oxygen concentration in the measured gas G whose oxygen concentration has been adjusted by the pump cell 41. The sensor cell 43 has the sensor electrode 23 provided on the measured-gas space 51-side surface 201 of the solid electrolyte body 2 and proximalward from the arrangement position of the pump electrode 21. The sensor cell 43 is configured to first measure the oxygen ion current flowing between the sensor electrode 23 and the reference electrode 25 and then measure a specific gas concentration based on the difference between the measured oxygen iron current and the oxygen ion current in the monitor cell 42.

As shown in FIG. 1, the heater 6 includes a heat-generating portion 62 that generates heat when supplied with electric current, and a pair of lead portions 63 that are respectively connected with a pair of end portions 622 of the heat-generating portion 62. The entire heat-generating portion 62 is arranged in the sensor protruding portion 100. A heat-generating center 601 of the heat-generating portion 62 is located distalward from a center 231 of the sensor electrode 23. The distance E from a distal end 101 of the sensor protruding portion 100 to the center 231 of the sensor electrode 23 is set to be in the range of 0.7 to 1.3 D, where D is the distance from the distal end 101 of the sensor protruding portion 100 to a proximal end 621 of the heat-generating portion 62. The distance F from the distal end 101 of the sensor protruding portion 100 to a center 211 of the pump electrode 21 is set to be in the range of 0.3 to 0.7 D.

Figure 6:
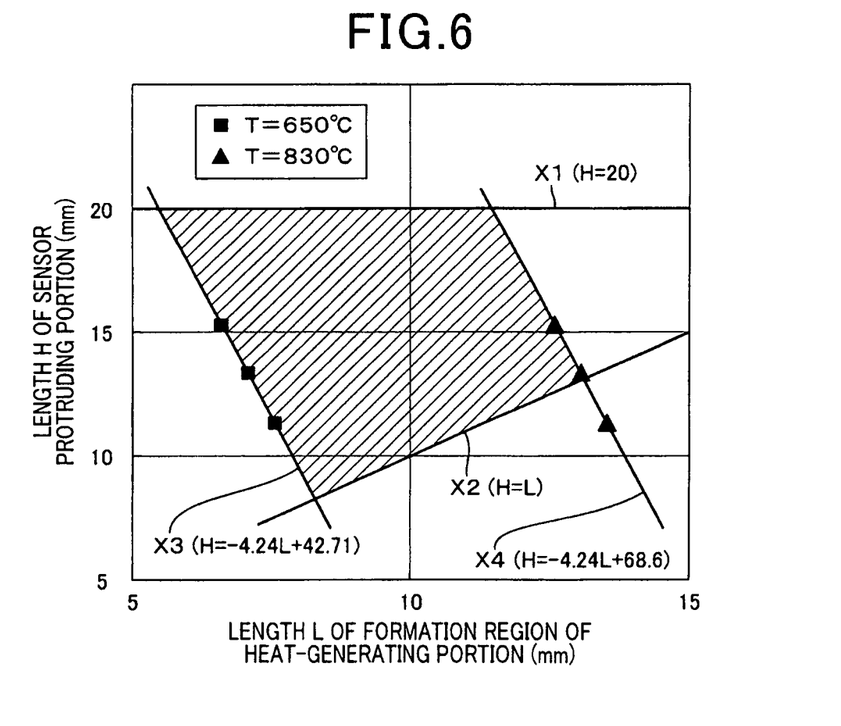
FIG. 6 is a graph illustrating the relationship between the length L of the formation region of the heat-generating portion and the length H of the sensor protruding portion in the gas sensor according to the example.

As shown in FIG. 6, the length L (in mm) of a formation region of the heat-generating portion 62 and the length H (in mm) of the sensor protruding portion 100 in the longitudinal direction M, in which the sensor protruding portion 100 protrudes from the holder 12, are set to be in a range that is enclosed by first to fourth reference lines X1-X4 on a two-dimensional coordinate plane whose horizontal and vertical axes respectively indicate the lengths L and H. The first reference line X1 represents the relationship of H=L. The second reference line X2 represents the relationship of H=20. The third reference line X3 represents the relationship of H=−4.24L+42.71. The fourth reference line X4 represents the relationship of H=−4.24L+68.6. In addition, the proximal end 621 of the heat-generating portion 62 denotes the boundary position where the heat-generating portion 62 is connected with the pair of lead portions 63. The center 231 of the sensor electrode 23 denotes the center of figure of the sensor electrode 23 in plan view. The center 211 of the pump electrode 21 denotes the center of figure of the pump electrode 21 in plan view.

Hereinafter, the configuration of the gas sensor 1 according to the present example will be described in more detail.

As shown in FIG. 4, the gas sensor 1 has a cover 13 that receives the sensor protruding portion 100 of the sensor structural body 10. The gas sensor 1 is configured so that the exhaust gas is introduced as the measured gas G to the sensor protruding portion 100 of the sensor structural body 10 via through-holes 131 provided in the cover 13. The gas sensor 1 is used after being arranged in an exhaust pipe of a motor vehicle. The measured gas G is the exhaust gas flowing in the exhaust pipe. The gas sensor 1 is used to sense the concentration of NOx (Nitrogen Oxides) as the specific gas in the exhaust gas.

The holder 12 is constituted of an insulator for holding the sensor structural body 10 in a housing 14 of the gas sensor 1. A proximal end portion of the sensor structural body 10 in the longitudinal direction M is embedded in the holder 12.

As shown in FIGS. 2 and 3, the pump electrode 21, the monitor electrode 22, the sensor electrode 23 and the reference electrode 25 are provided with respect to the single solid electrolyte body 2. On the measured-gas space 51-side surface 201 of the solid electrolyte body 2, there is stacked an insulator 31 for forming the measured-gas space 51 via a first spacer 311 that is electrically insulative. On the reference-gas space 52-side surface 202 of the solid electrolyte body 2, there is stacked the heater 6 for heating the solid electrolyte body 2 via a second spacer 33 that is electrically insulative.

The heat-generating portion 62 and the pair of lead portions 63 in the heater 6 are sandwiched between a pair of ceramic substrates 61 that are electrically insulative. As shown in FIG. 1, the heat-generating portion 62 has a shape of meandering in the longitudinal direction M of the sensor structural body 10. The cross-sectional area of the heat-generating portion 62 is less than the cross-sectional area of each of the lead portions 63. Here, the cross-sectional areas of the heat-generating portion 62 and the lead portions 63 are respectively the areas of cross-sections of the heat-generating portion 62 and the lead portions 63 perpendicular to the direction in which electric current flows. Moreover, the cross-sectional area of the heat-generating portion 62 is substantially constant over the entire length of the meandering heat-generating portion 62. When electric current is supplied to the pair of lead portions 63, the heat-generating portion 62 generates Joule heat. The heat-generating center 601 of the heat-generating portion 62 is at the central position of the heat-generating portion 62 and the sensor element 11 in the width direction, and at substantially the central position of the heat-generating portion 62 in the longitudinal direction M.

Moreover, the heat-generating portion 62 and the lead portions 63 are formed by being separately printed on the ceramic substrates 61. Therefore, the heat-generating portion 62 and the lead portions 63 partially overlap each other.

As shown in FIG. 2, the sensor structural body 10 has a long shape and is configured to introduce the measured gas G from the distal side in the longitudinal direction M. The diffusion-resistant body 32 is embedded in an introduction port 312 of the measured gas G formed in a distal end portion of the first spacer 311 in the longitudinal direction M. The diffusion-resistant body 32 is formed of a porous material having a property of allowing gases to permeate therethrough. The diffusion-resistant body 32 is provided to introduce the measured gas G into the measured-gas space 51 at a predetermined diffusion rate. The flow direction N of the measured gas G in the sensor element 11 coincides with the longitudinal direction M toward the proximal side from the distal side.

The pump cell 41 has a voltage applying means for applying a voltage between the pump electrode 21 and the reference electrode 25. The monitor cell 42 has an electric current measuring means for measuring electric current flowing between the monitor electrode 22 and the reference electrode 25. The sensor cell 43 has an electric current measuring means for measuring electric current flowing between the sensor electrode 23 and the reference electrode 25.

As shown in FIGS. 2 and 3, the solid electrolyte body 2 is a substrate of zirconia having oxygen ion conductivity. In the present example, the reference electrode 25 is provided, as a common reference electrode to the pump electrode 21, the monitor electrode 22 and the sensor electrode 23, at such a position as to overlap these electrodes 21-23 in a thickness direction of the solid electrolyte body 2. In addition, separate reference electrodes 25 may be provided for the pump electrode 21, the monitor electrode 22 and the sensor electrode 23.

The pump electrode 21 is formed of a Pt—Au alloy which is a material having the property of decomposing oxygen. The monitor electrode 22 and the reference electrode 25 are formed of Pt which is a material having the property of decomposing oxygen. The sensor electrode 23 is formed of a Pt—Rh alloy which is a material having the property of decomposing NOx. Moreover, each of the electrodes 21, 22, 23 and 25 also contains zirconia which is a common material to the solid electrolyte body 2.

The content of Au in the Pt—Au alloy forming the pump electrode 21 may be set to be lower than or equal to 20% in mass. The content of Rh in the Pt—Rh alloy forming the sensor electrode 23 may be set to be lower than or equal to 80% in mass.

Moreover, as shown in FIG. 1, that portion of the holder 12 which holds the sensor structural body 10 is formed into the shape of a cylinder having a diameter d in the range of 5 to 12 mm. The diameter d of the portion of the holder 12 holding the sensor structural body 10 may be determined based on the relationship with the width of the sensor structural body 10.

Figure 7:
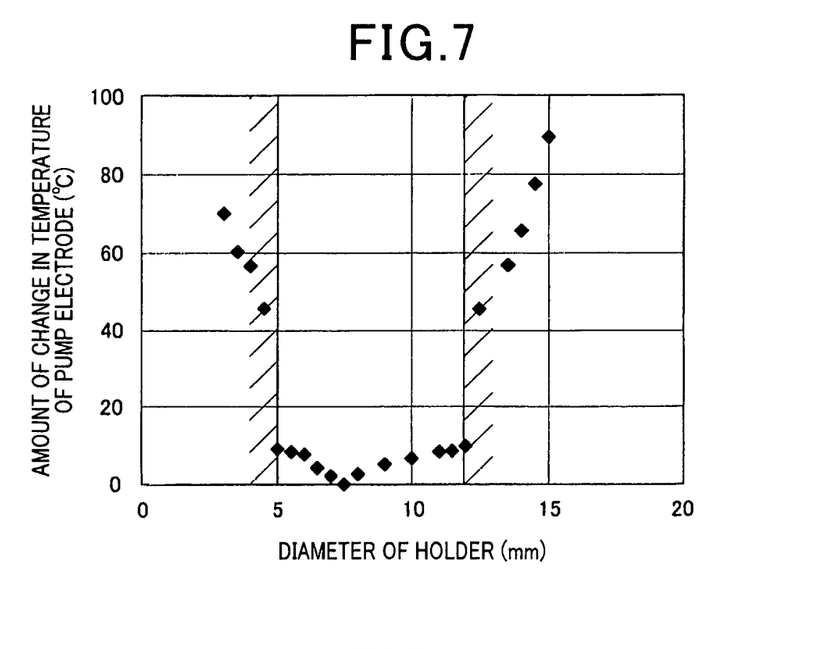
FIG. 7 is a graph illustrating the relationship between the diameter of a holder and the amount of change in the temperature of a pump electrode in the gas sensor according to the example.

FIG. 7 illustrates the relationship between the diameter d (in mm) of the holder 12 and the amount of change (in ° C.) in the temperature (average temperature) of the pump electrode 21 in the sensor element 11. When the dimeter d of the holder 12 was equal to 7.5 mm, the temperature of the pump electrode 21 was defined as a reference temperature and the amount of change in the temperature of the pump electrode 21 was represented by 0 (° C.). When the diameter d of the holder 12 was changed from 7.5 mm, the amount of change in the temperature of the pump electrode 21 was represented by the temperature difference (° C.) obtained by subtracting the reference temperature from the then temperature of the pump electrode 21.

As can be seen from FIG. 7, when the diameter d of the holder 12 was in the range of 5 to 12 mm, no large changes occurred in the temperature of the pump electrode 21. In comparison, when the diameter d of the holder 12 was greater than 12 mm, the heat transfer from the sensor structural body 10 to the holder 12 was increased and thus the temperature of the pump electrode 21 was lowered. On the other hand, when the diameter d of the holder 12 was less than 5 mm, the heat transfer from the sensor structural body 10 to the holder 12 was reduced and thus the temperature of the pump electrode 21 was increased.

From the above results, it has been made clear that the influence of the size of the holder 12 on the temperature of the pump electrode 21 can be lowered by setting the dimeter d of the holder 12 to be in the range of 5 to 12 mm. In addition, the tendencies of FIG. 7 were similarly seen in the sensor electrode 23 or the like other than the pump electrode 21. Therefore, it is possible to lower the influence of the size of the holder 12 on the temperatures of the pump cell 41 and the sensor cell 43 by setting the dimeter d of the holder 12 to be in the range of 5 to 12 mm.

The gas sensor 1 according to the present example is configured to keep the temperature of the pump electrode 21 in the range of 740 to 920° C. and the temperature of the sensor electrode 23 in the range of 650 to 830° C. when the sensor element 11 is heated by the heater 6. The temperature of the pump electrode 21 and the temperature of the sensor electrode 23 are determined by the temperature of the heater 6. To keep the temperature of the pump electrode 21 in the range of 740 to 920° C. and the temperature of the sensor electrode 23 in the range of 650 to 830° C., the temperature of the heater 6 may be set to be in the range of 710 to 890° C.

The distance from the center 211 of the pump electrode 21 to the heat-generating center 601 of the heater 6 is shorter than the distance from the center 231 of the sensor electrode 23 to the heat-generating center 601 of the heater 6. Moreover, the distance from the center 221 of the monitor electrode 22 to the heat-generating center 601 of the heater 6 is substantially equal to the distance from the center 231 of the sensor electrode 23 to the heat-generating center 601 of the heater 6. Thus, the pump electrode 21 is heated to a higher temperature than the monitor electrode 22 and the sensor electrode 23.

In addition, the temperature of the pump cell 41 composed of the pump electrode 21, the solid electrolyte body 2 and the reference electrode 25 is considered to be equal to the temperature of the pump electrode 21. Similarly, the temperatures of the monitor cell 42 and the sensor cell 43 are respectively considered to be equal to the temperatures of the monitor electrode 22 and the sensor electrode 23.

Figure 8:
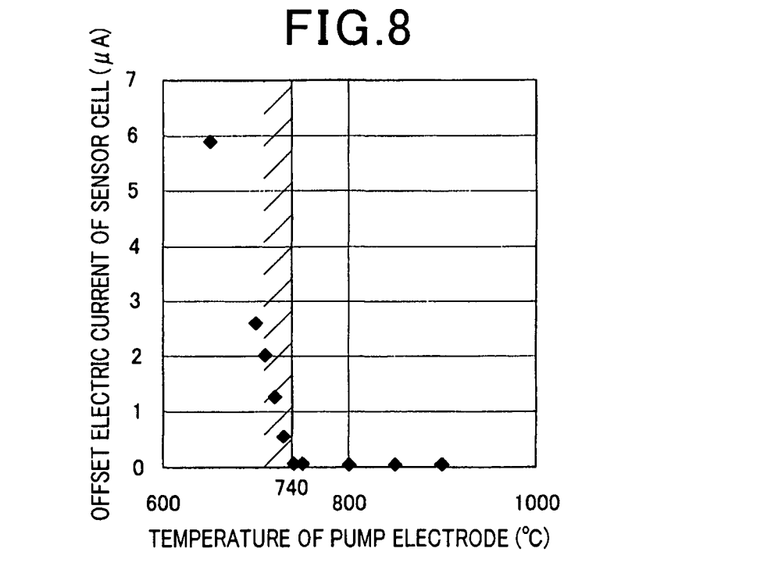
FIG. 8 is a graph illustrating the relationship between the temperature of the pump electrode and the offset electric current of a sensor cell in the gas sensor according to the example.

FIG. 8 illustrates the relationship between the temperature (in ° C.) of the pump electrode 21 and the offset electric current (in µA) flowing in the sensor cell 43. The offset electric current flowing in the sensor cell 43 denotes the oxygen ion current flowing in the sensor cell 43 when the concentration of NOx in the measured-gas space 51 is equal to zero.

As can be seen from FIG. 8, the offset electric current flowing in the sensor cell 43 increased as the temperature of the pump electrode 21 dropped below 740° C. The reason is that with the drop in the temperature of the pump electrode 21, the pump cell 41 became unable to sufficiently exhaust oxygen, increasing the residual oxygen in the measured-gas space 51.

Figure 9:
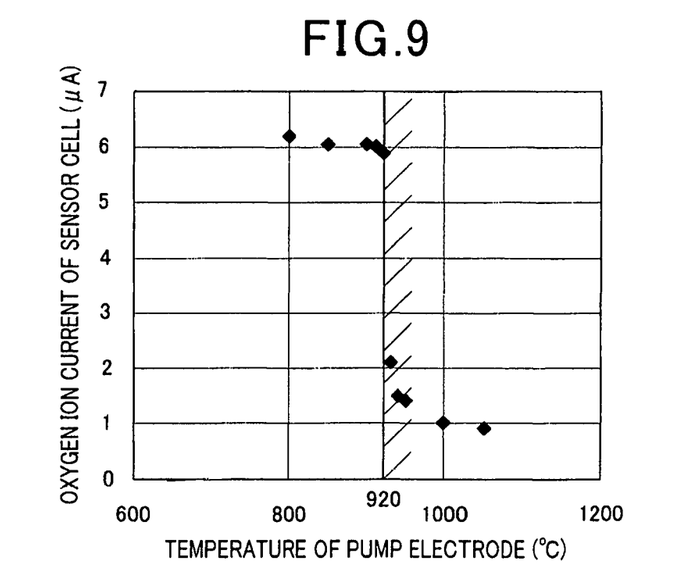
FIG. 9 is a graph illustrating the relationship between the temperature of the pump electrode and the oxygen ion current of the sensor cell in the gas sensor according to the example.

FIG. 9 illustrates the relationship between the temperature (in ° C.) of the pump electrode 21 and the oxygen ion current (in µA) flowing in the sensor cell 43 during the sensing of a predetermined concentration of NOx.

As can be seen from FIG. 9, the oxygen ion current flowing in the sensor cell 43 decreased as the temperature of the pump electrode 21 increased above 920° C. The reason is that with the increase in the temperature of the pump electrode 21, NOx was decomposed at the pump cell 41, reducing NOx in the measured-gas space 51.

Accordingly, it has been made clear that the accuracy of sensing the concentration of NOx by the gas sensor 1 can be kept high by keeping the temperature of the pump electrode 21 in the range of 740 to 920° C. Moreover, as will be described later, to prevent the sensor electrode 23 from being poisoned by Au, it is preferable to keep the temperature of the pump electrode 21 in the range of 740 to 850° C.

Figure 10:
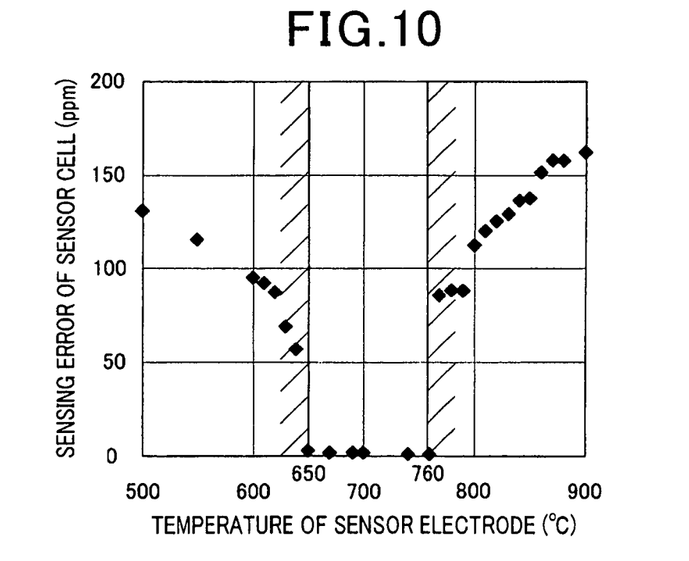
FIG. 10 is a graph illustrating the relationship between the temperature of the sensor electrode and the sensing error of the sensor cell in the gas sensor according to the example.

FIG. 10 illustrates the relationship between the temperature (in ° C.) of the sensor electrode 23 and the error (in ppm) in sensing the concentration of NOx by the sensor cell 43.

As can be seen from FIG. 10, when the temperature of the sensor electrode 23 was in the range of 650 to 760° C., almost no error occurred in the accuracy of sensing the concentration of NOx by the sensor cell 43. In comparison, as the temperature of the sensor electrode 23 increased above 760° C., Au in the Pt—Au alloy forming the pump electrode 21 came to disperse to poison the sensor electrode 23, thereby lowering the NOx activity at the sensor cell 43 and thus increasing the error in sensing the concentration of NOx. On the other hand, when the temperature of the sensor electrode 23 dropped below 650° C., the sensor cell 43 could not be heated to a temperature at which the sensor cell 43 exhibits the NOx activity, thus increasing the error in sensing the concentration of NOx.

Figure 11:
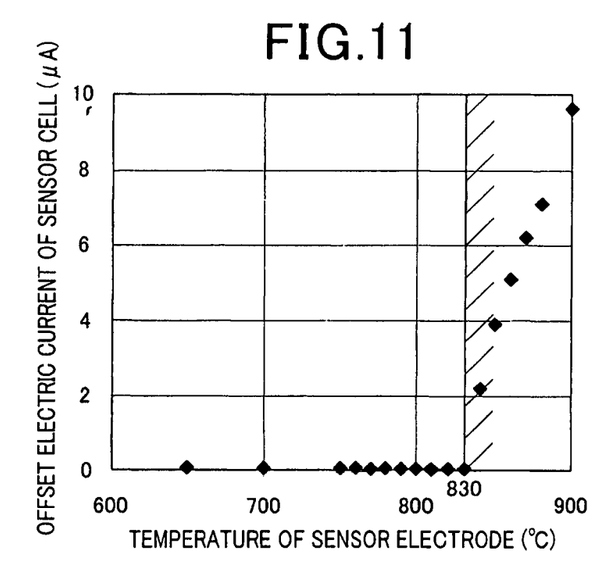
FIG. 11 is a graph illustrating the relationship between the temperature of the sensor electrode and the offset electric current of the sensor cell in the gas sensor according to the example.

FIG. 11 illustrates the relationship between the temperature (in ° C.) of the sensor electrode 23 and the offset electric current (in μA) flowing in the sensor cell 43. The offset electric current flowing in the sensor cell 43 denotes the oxygen ion current flowing in the sensor cell 43 when the concentration of NOx in the measured-gas space 51 is equal to zero.

As can be seen from FIG. 11, the offset electric current flowing in the sensor cell 43 increased as the temperature of the sensor electrode 23 increased above 830° C. The reason is that with the increase in the temperature of the sensor electrode 23, moisture in the measured-gas space 51 was decomposed at the sensor cell 43.

Accordingly, it has been made clear that the accuracy of sensing the concentration of NOx by the gas sensor 1 can be kept high by keeping the temperature of the sensor electrode 23 in the range of 650 to 830° C. Moreover, to prevent the sensor electrode 23 from being poisoned by Au, it is preferable to keep the temperature of the sensor electrode 23 in the range of 650 to 760° C.

The relationship in length between the heat-generating portion 62 and the sensor protruding portion 100 in the gas sensor 1 is determined as follows.

As shown in FIG. 6, the length L (in mm) of the formation region of the heat-generating portion 62 and the length H (in mm) of the sensor protruding portion 100 are determined to satisfy the relational expression of L ≤H≤20. The relational expression of L≤H is derived from the configuration where the entire heat-generating portion 62 is arranged in the sensor protruding portion 100. That is, the entire length L (in mm) of the formation region of the heat-generating portion 62 is less than or equal to the length H (in mm) of the sensor protruding portion 100.

Moreover, when the length H (in mm) of the sensor protruding portion 100 is too large, the probability of the sensor protruding portion 100 being broken becomes high. The relational expression of H≤20 is a condition for preventing the sensor protruding portion 100 from being broken.

The third reference line X3 representing the relationship of H=−4.24L+42.71 and the fourth reference line X4 representing the relationship of H=−4.24L+68.6 are obtained as follows.

Figure 5:
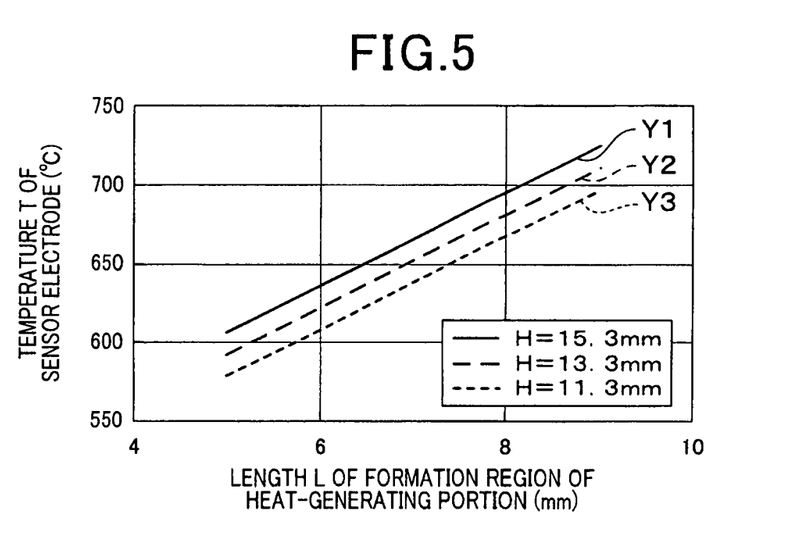
FIG. 5 is a graph illustrating the relationship between the length L of a formation region of a heat-generating portion and the temperature of a sensor electrode in the gas sensor according to the example.

First, as shown in FIG. 5, with the temperature of the pump electrode 21 set to 740° C., the relationship between the length L (in mm) of the formation region of the heat-generating portion 62 and the temperature T (in ° C.) of the sensor electrode 23 are determined. Moreover, this relationship is determined varying the length H (in mm) of the sensor protruding portion 100 to be 15.3 mm, 13.3 mm and 11.3 mm. Consequently, relational lines Y1, Y2 and Y3 are obtained by linear regression respectively for the cases where the length H (in mm) of the sensor protruding portion 100 is respectively equal to 15.3 mm, 13.3 mm and 11.3 mm.

As a result, the length L (in mm) of the formation region of the heat-generating portion 62 and the temperature T (in ° C.) of the sensor electrode 23 are in a proportional relationship so that the greater the length L (in mm) of the formation region of the heat-generating portion 62, the higher the temperature T (in ° C.) of the sensor electrode 23. This result is simply based on the fact that the longer the heat-generating portion 62, the more heat is generated by the heat-generating portion 62. Moreover, the greater the length H (in mm) of the sensor protruding portion 100, the higher the temperature of the sensor electrode 23. This result is based on the fact that the greater the length H of the sensor protruding portion 100, the less heat is transferred from the sensor structural body 10 to the holder 12.

Further, for the cases where the length H (in mm) of the sensor protruding portion 100 is respectively equal to 15.3 mm, 13.3 mm and 11.3 mm, the length L (in mm) of the formation region of the heat-generating portion 62 when the temperature of the sensor electrode 23 is equal to 650° C. is substituted into the respective relational lines Y1, Y2 and Y3, thereby obtaining the third reference line X3 representing the relationship of H=−4.24L+42.17. Moreover, for the cases where the length H (in mm) of the sensor protruding portion 100 is respectively equal to 15.3 mm, 13.3 mm and 11.3 mm, the length L (in mm) of the formation region of the heat-generating portion 62 when the temperature of the sensor electrode 23 is equal to 830° C. is substituted into the respective relational lines Y1, Y2 and Y3, thereby obtaining the fourth reference line X4 representing the relationship of H=−4.24L+68.6.

As above, the relationship between the length L (in mm) of the formation region of the heat-generating portion 62 and the length H (in mm) of the sensor protruding portion 100 in the gas sensor 1 is determined by the first to the fourth reference lines X1, X2, X3 and X4 respectively representing the relationships of H=L, H=20, H=−4.24L+42.71 and H=−4.24L+68.6. That is, it is possible to keep the temperature of the pump electrode 21 in the suitable range of higher than or equal to 740° C. and the temperature of the sensor electrode 23 in the suitable range of 650 to 830° C. by setting the length L (in mm) of the formation region of the heat-generating portion 62 and the length H (in mm) of the sensor protruding portion 100 within the range enclosed by the reference lines X1, X2, X3 and X4 on the two-dimensional coordinate plane whose horizontal and vertical axes respectively indicate the lengths L and H.

In addition, if the positional relationship between the length L (in mm) of the formation region of the heat-generating portion 62 and the length H (in mm) of the sensor protruding portion 100 is in the range leftward from the third reference line X3, it becomes impossible to keep the temperature of the sensor cell 43 higher than or equal to 650° C.

On the other hand, if the positional relationship between the length L (in mm) of the formation region of the heat-generating portion 62 and the length H (in mm) of the sensor protruding portion 100 is in the range rightward from the fourth reference line X4, it becomes impossible to keep the temperature of the sensor cell 43 lower than or equal to 830° C.

Moreover, when heated by the heater 6, both the temperature of the pump electrode 21 and the temperature of the sensor electrode 23 increase in proportion to the amount of heating by the heater 6. The temperature of the pump electrode 21 is proportional to the temperature of the sensor cell 43. Specifically, the temperature of the pump electrode 21 is substantially equal to 740° C. when the temperature of the sensor electrode 23 becomes equal to 650° C., and substantially equal to 920° C. when the temperature of the sensor electrode 23 becomes equal to 830° C.

Therefore, it is possible to have the temperature of the pump electrode 21 in the range of 740 to 920° C. by setting the length L (in mm) of the formation region of the heat-generating portion 62 and the length H (in mm) of the sensor protruding portion 100 so as to have the temperature of the sensor electrode 23 in the range of 650 to 830° C.

Accordingly, the gas sensor 1 according to the present example can suitably control the temperatures of the pump cell 41 and the sensor cell 43.

Figure 12:
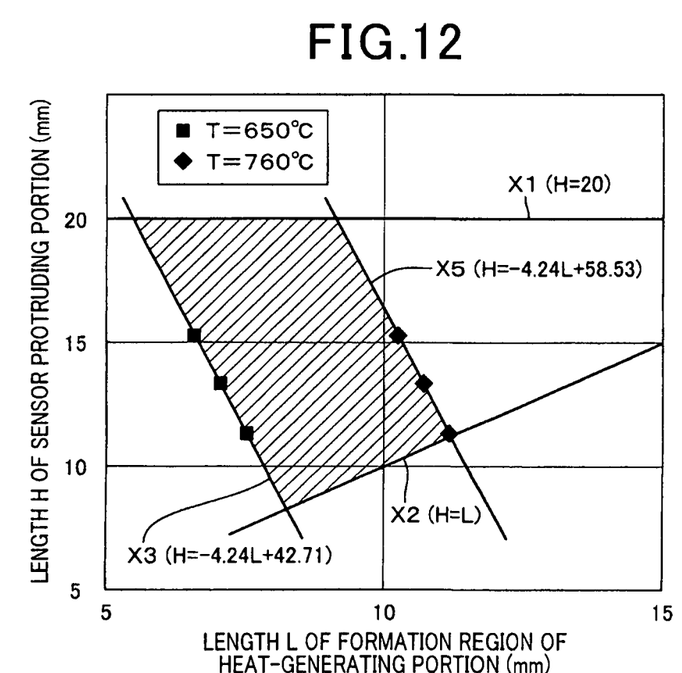
FIG. 12 is a graph illustrating the relationship between the length L of the formation region of the heat-generating portion and the length H of the sensor protruding portion in the gas sensor according to the example.

Moreover, as shown FIG. 12, it is more preferable to set the length L (in mm) of the formation region of the heat-generating portion 62 and the length H (in mm) of the sensor protruding portion 100 to be in a range that is enclosed by the first reference line X1, the second reference line X2, the third reference line X3 and a fifth reference line X5 on the two-dimensional coordinate plane whose horizontal and vertical axes respectively indicate the lengths L and H. The first reference line X1 represents the relationship of H=L. The second reference line X2 represents the relationship of H=20. The third reference line X3 represents the relationship of H=−4.24L+42.71. The fifth reference line X5 represents the relationship of H=−4.24L+58.53.

Similar to the third reference line X3 and the fourth reference line X4, the fifth reference line X5 representing the relationship of H=−4.24L+58.53 is obtained by substituting, for the cases where the length H (in mm) of the sensor protruding portion 100 is respectively equal to 15.3 mm, 13.3 mm and 11.3 mm, the length L (in mm) of the formation region of the heat-generating portion 62 when the temperature of the sensor electrode 23 is equal to 760° C. into the respective relational lines Y1, Y2 and Y3. Moreover, the temperature of the pump electrode 21 is proportional to the temperature of the sensor cell 43; the temperature of the pump electrode 21 is substantially equal to 850° C. when the temperature of the sensor electrode 23 becomes equal to 760° C.

In this case, it is possible to keep the temperature of the pump electrode 21 in the suitable range of 740 to 850° C. and the temperature of the sensor electrode 23 in the suitable range of 650 to 760° C. Moreover, it is also possible to prevent the sensor electrode 23 from being poisoned by Au in the Pt—Au alloy forming the pump electrode 21.

DESCRIPTION OF REFERENCE SIGNS

1: gas sensor
10: sensor structural body
100: sensor protruding portion
11: sensor element
12: holder
2: solid electrolyte body
21: pump electrode
23: sensor electrode
25: reference electrode
32: diffusion-resistant body
41: pump cell
43: sensor cell
51: measured-gas space
52: reference-gas space
6: heater
62: heat-generating portion
63: lead portions
G: measured gas
A: reference gas
M: longitudinal direction

The invention claimed is:

1. A gas sensor having a sensor structural body formed by stacking a sensor element and a heater and a holder holding the sensor structural body, the gas sensor being configured so that a sensor protruding portion of the sensor structural body protrudes distalward from the holder so as to be exposed to a measured gas, wherein the sensor element comprises:

a solid electrolyte body having oxygen ion conductivity;

a measured-gas space which is formed on one side of the solid electrolyte body and into which the measured gas is introduced via a diffusion-resistant body;

a reference-gas space which is formed on the other side of the solid electrolyte body and into which a reference gas is introduced;

a pump cell having a pump electrode provided on a measured-gas space side surface of the solid electrolyte body and being configured to adjust the concentration of oxygen in the measured-gas space by applying a voltage between the pump electrode and a reference electrode provided on a reference-gas space side surface of the solid electrolyte body; and a sensor cell having a sensor electrode provided on the measured-gas space side surface of the solid electrolyte body and proximalward from the arrangement position of the pump electrode, the sensor cell being configured to measure oxygen ion current flowing between the sensor electrode and the reference electrode, wherein the heater comprises a heat-generating portion that generates heat when supplied with electric current, and a pair of lead portions that are respectively connected with a pair of end portions of the heat-generating portion, the entire heat-generating portion is arranged in the sensor protruding portion, a heat-generating center of the heat-generating portion is located distalward from a center of the sensor electrode, a distance E from a distal end of the sensor protruding portion to the center of the sensor electrode is in a range of 0.7D to 1.3D and a distance F from the distal end of the sensor protruding portion to a center of the pump electrode is in a range of 0.3D to 0.7D, where D is a distance from the distal end of the sensor protruding portion to a proximal end of the heat-generating portion, and a length L in mm where the heat-generating portion is formed and a length H in mm of the sensor protruding portion in a longitudinal direction, in which the sensor protruding portion protrudes from the holder, are set to be in a range that is enclosed by first to fourth reference lines on a two-dimensional coordinate plane whose horizontal and vertical axes respectively indicate the lengths L and H, the first reference line representing a relationship of H=L, the second reference line representing a relationship of H=20, the third reference line representing the relationship of H=−4.24L+42.71, the fourth reference line representing the relationship of H=−4.24L+68.6.

2. The gas sensor as set forth in claim 1, wherein the length L where the heat-generating portion is formed and the length H of the sensor protruding portion in the longitudinal direction, in which the sensor protruding portion protrudes from the holder, are set to be in a range that is enclosed on the two-dimensional coordinate plane by the first reference line representing the relationship of H=L, the second reference line representing the relationship of H=20, the third reference line representing the relationship of H=−4.24L+42.71 and a fifth reference line representing the relationship of H=−4.24L+58.53.

3. The gas sensor as set forth in claim 1, wherein the pump electrode contains a Pt—Au alloy, and the sensor electrode contains a Pt—Rh alloy.

4. The gas sensor as set forth in claim 1, wherein a portion of the holder which holds the sensor structural body is formed into the shape of a cylinder having a diameter in a range of 5 to 12mm.

* * * * *